United States Patent
Gabor et al.

(10) Patent No.: US 9,699,975 B2
(45) Date of Patent: *Jul. 11, 2017

(54) **TOMATO PLANTS THAT EXHIBIT RESISTANCE TO *BOTRYTIS CINEREA***

(71) Applicants: Seminis Vegetable Seeds, Inc., St. Louis, MO (US); Cornell Research Foundation, Inc., Ithaca, NY (US)

(72) Inventors: Brad Kane Gabor, Woodland, CA (US); Anna Julia Frampton, Davis, CA (US); Mauro Bragaloni, Latine (IT); Steven D. Tanksley, Ithaca, NY (US)

(73) Assignees: Seminis Vegetable Seeds, Inc., St. Louis, MO (US); CORNELL RESEARCH FOUNDATION, INC., Ithaca, NY (US)

( * ) Notice: Subject to any disclaimer, the term of this patent is extended or adjusted under 35 U.S.C. 154(b) by 219 days.

This patent is subject to a terminal disclaimer.

(21) Appl. No.: 14/549,152

(22) Filed: Nov. 20, 2014

(65) Prior Publication Data

US 2015/0082477 A1   Mar. 19, 2015

Related U.S. Application Data

(60) Continuation of application No. 12/816,898, filed on Jun. 16, 2010, now Pat. No. 8,895,803, which is a division of application No. 10/278,360, filed on Oct. 23, 2002, now Pat. No. 7,799,976, which is a continuation-in-part of application No. 10/131,156, filed on Apr. 24, 2002, now abandoned.

(60) Provisional application No. 60/286,296, filed on Apr. 25, 2001.

(51) Int. Cl.
  *C12Q 1/68* (2006.01)
  *A01H 1/04* (2006.01)
  *A01H 5/08* (2006.01)

(52) U.S. Cl.
  CPC ........... *A01H 1/04* (2013.01); *A01H 5/08* (2013.01); *C12Q 1/6895* (2013.01); *C12Q 2600/13* (2013.01); *C12Q 2600/156* (2013.01)

(58) Field of Classification Search
  None
  See application file for complete search history.

(56) References Cited

U.S. PATENT DOCUMENTS

| 5,304,719 A | 4/1994 | Segebart |
| 5,367,109 A | 11/1994 | Segebart |
| 5,763,755 A | 6/1998 | Carlone |
| 5,850,009 A | 12/1998 | Kevern |

OTHER PUBLICATIONS

Bernacchi et al., Advanced Backcross QTL analysis in tomatato. I. Identification of QTLs for traits of agronomic importance from Lycopersicon hirsutum, *Theoretical and Applied Genetics*, 97(3):381-397 (1998).
Bernacchi et al., "Advanced backcross QTL analysis of tomato. II. Evaluation of near-isogenic lines carrying single-donor introgression of rdesirable wild QTL-alleles derived from Lycopersiscon hirsutum and L. pimpinellifolium," *Theoretical and Applied Genetics*, 97(1-2):170-180 (1998).
Bernatzky et al., "Toward a saturated linkage map in tomato based on isozymes and random cDNA sequences," *Genetics*, 112:887-898 (1986).
Chen et al., "A Molecular Linkage Map of Tomato based on a Cross Between Lycopericon esculentum and L. Pimpinellifolium and its Comparison with Other Molecular Maps of Tomato," *Genome*, 1:94-103 (1999).
Chetelat et al., "A male-fertile Lycopersicon esculetum x Solanum lycopersicoides hybrid enables direct backcrossing to tomato at the diploid level," *Euphytica*, 95(1):99-108 (1997).
Chetelat et al., "Tolerance to Botrytis cinerea," *Acta Horticulturae*, 487:313-316 (1999).
Concibido et al., "Genome Mapping of Soybean Cyst Nematode Resistance Genes in 'Peking', PI 90763, PI 88788 Using DNA Markers," *Crop Sci.*, 37:258-264 (1997).
Dekkers et al., "The use of molecular genetics in the improvement of agricultural populations," *Nature Reviews | Genetics*, 3:22-32 (2002).
Doganlar et al., "Molecular mapping of a py-l gene for resistance of corky root rot (*Pyrenochaeta lycopersici*) in tomato," *Theortical and Applied Genetics*, 97(5-6):784-788 (1998).
Egashira et al., "Screening of Wild Accession Resistant to Gray Mold (*Botrytis cinerea* Pers.) ub Lycopercon," *Acta Plysiol. Plant*, 22(3):324-326 (2000).
Farooq et al., "Molecular Markers in Plant Breeding-I: Concepts and Characterizations," *Pakistan Journal of Biological Sciences*, 5(10):1135-1140 (2002).
Finkers et al., "The construction of a Solanum habrochaites LYC4 introgression line population and the identification of QTLs for resistance to Botrytis cinerea ," *Theoretical and Applied Genetics*, 114:1071-1080 (2007).
Finkers et al., "Three QTL's for Botrytis cinerea Resistance in Tomato," *Theoretical and Applied Genetics*, 114:585-593 (2007).
Fulton et al., "Advanced backcross QTL analysis of Lycoperiscon esculentum X Lycoperiscon parviflorum cross," *Theoretical and Applied Genetics*, 100(7):1025-1042 (2000).
Fulton et al., "Identification, Analysis, and Utilization of Conserved Ortholog Set Markers for Comparative Genomics in Higher Plants", *The Plant Cell*, 14:1457-1467 (2002).

(Continued)

*Primary Examiner* — David T Fox
(74) *Attorney, Agent, or Firm* — Arnold & Porter Kaye Scholer LLP; Alissa M. Eagle; David R. Marsh

(57) ABSTRACT

The present invention relates to tomato plants that exhibit resistance to *Botrytis cinerea* and methods for developing new inbreds, hybrid, apomictic and genetically engineered tomato plants that possess resistance to *Botrytis cinerea* and having commercially desirable characteristics.

18 Claims, 2 Drawing Sheets

(56) References Cited

OTHER PUBLICATIONS

Figure 1:
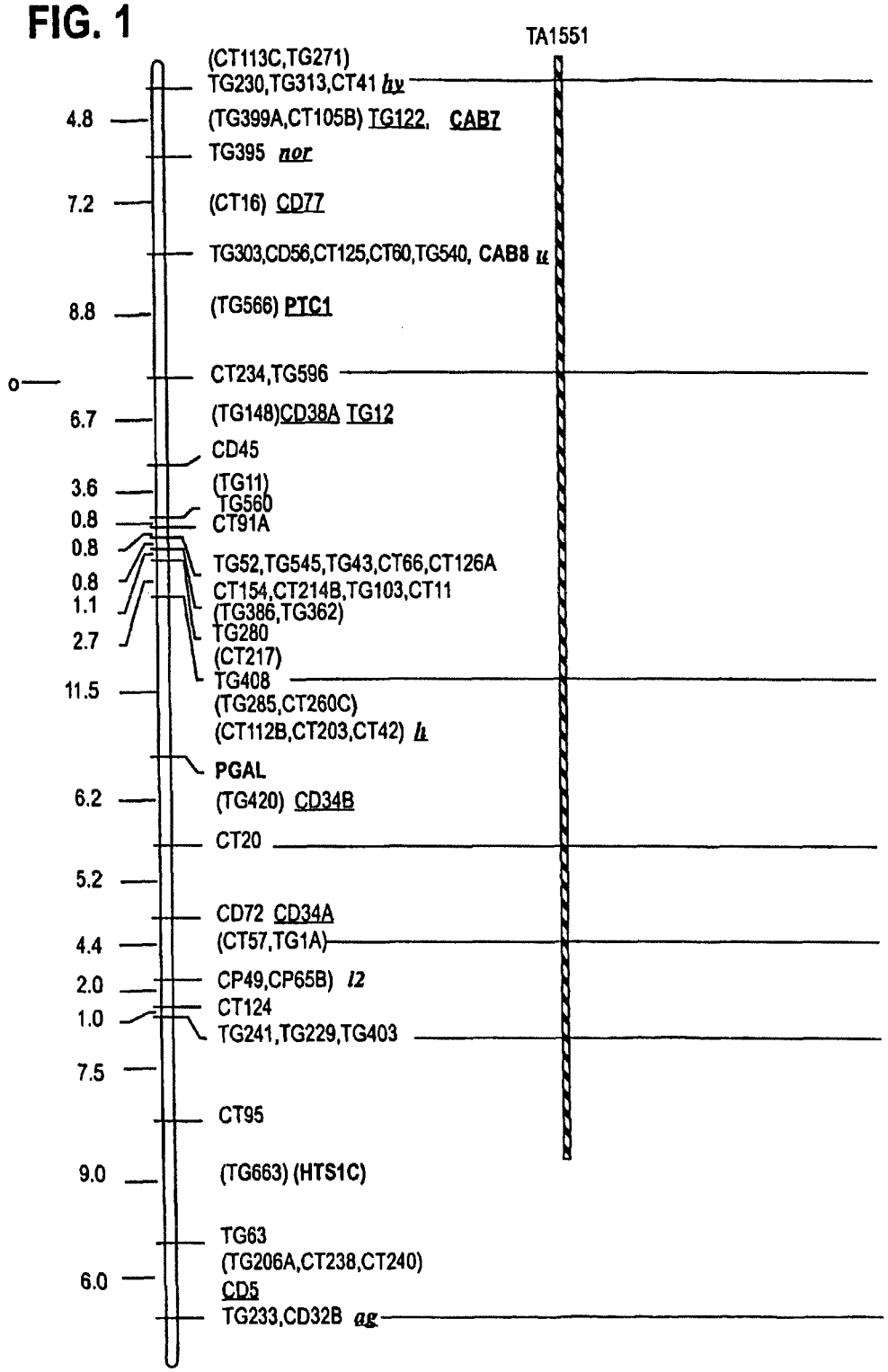

Grandillo et al., "QTL analysis of horticultural traits differentiating the cultivated tomato from the closely related species *Lycoperscion pimpinellifolium,*" *Theor Appl Genet*, 92:935-951 (1996).
Grube et al., "Comparative Genetics of Disease Resistance Within the Solanaceae," *Genetics*, 155:873-887 (2000).
Gupta et al., "Molecular markers and their applications in wheat breeding," *Plant Breeding*, 118:369-390 (1999).
Hayes et al., "Quantitative trait locus effects and environmental interaction in a simple of North American barley germ plasm," *Theoretical and Applied Genetics*, 87:392-401 (1993).
Huang et al., "Development of diagnostic PCR markers closely linked to the tomato powdery mildew resistance gene Ol-l on chromosome 6 of tomto," *Theor. Appl. Genet.*, 101:918-924 (2000).
Ignatova et al., "Resistance of Tomato Fl Hybrids to Grey Mold," *Acta Physiolo. Plant*, 22(3):326-328 (2000).
Kerr et al., "Resistance to Cladosporium fulvum CKE. Obtained from Wild Species of Tomato," *Can. J. Botany*, 42:1541-1558 (1964).
Klinger et al., "Mapping of Cotton-Melon Aphid Resistance in Melon," *J. Amer. Soc. Hort. Sci.*, 126(1):56-63 (2001).
Lee et al., "Identification of quantitative trait loci for plant height, lodging, and maturity in a soybean population segregating for growth habit," *Theor. Appl. Genet.*, 92:516-523 (1996).
Michelmore et al., "Identification of markers linked to disease-resistance genes by bulked segregant analysis: a rapid method to detect markers in specific genomic regions by using segregating populations," *Proc. Natl. Acad. Sci.*, 88:9828-9832 (1991).
Mohan et al., "Genome mapping, molecular markers and marker-assisted selection in crop plants," *Molecular Breeding*, 3:87-103 (1997).
Monforte et al., "Developmet of a set of near isogenic and backcross recombinant inbred lines containing most of the Lycopersicon hirsutum genome in a L. esculetum genetic background: A tool for gene mapping and gene discovery," *Genome*, 43:803-813(2000).
Moreau et al., "Genetic Mapping of Ph-2, a Single Locus Controlling Partial resistance to Phytophthora infestans in tomato," *MPMI*, 11(4):259-269 (1998).
Nelson, "QGENE: software for marker-based genomic analysis and breeding," *Molecular Breeding*, 3:239-245 (1997).

International Search Report dated Jan. 8, 2003, as received in International Application No. PCT/US2002/012741.
International Search Report dated May 11, 2004, as received in International Application No. PCT/US2003/012256.
Petterson et al., "Predictability of heterozygosity scores and polymorphism information content values for rat genetic markers," *Mammalian Genome*, 6:512-520 (1995).
Ribaut et al., "Marker-assisted selection: new tools and strategies," *Trends in Plant Science*, 3(6):236-239 (1998).
Segal et al., "Correlation of genetic and physical structure in the region surrounding the I.sub.2 Fusarium oxysporum resistance locus in tomato," *Mol. Gen. Genet.*, 231:179-185 (1992).
Stamova et al., "Inheritance and genetic mapping of cucumber mosaic virus resistance introgressed from Lycopersicon chilense into tomato," *Theor. Appl. Genet.*, 101:527.537 (2000).
Supplemental European Search Report dated Jul. 22, 2004, as received in European Patent Application No. Application No. 02 72 5774.
Tanksley et al., "High Density Molecular Linkage Maps of the Tomato and Potato Genomes," *Genetics*, 132:1141-1160 (1992).
Tanksley et al., "Advanced backcross QTL analysis in a cross between an elite processing line of tomato and its wild relative *L. pimpinellifolium,*" *Theor Appl Genet*, 92:213-224 (1996).
Tanksley, "Molecular Markers in Plant Breeding," *Plant Molecular Biology Reporter*, 1(1):3-8 (1983).
Urbasch, "Resistance of Different Cultivated and Wild Tomato Plants *Lycopersicon*—SPP to *Botrytis cinerea,*" *J. Phytopathology*, 116(4):344-351 (1986).
Van Ooijen et al., "An RFLP Linkage Map of Lycopersicon peruvianum," *Theor. Appl. Genet.*, 89(7-8):1007-1013 (1994).
Vidaysky et al., "Tomato breeding lines resistance and tolerant to tomato yellow leaf curl virus issued from Lycopersicon hirsutum," *Phytopathology*, 88(9):910-914 (1998).
Westman et al., "potential for cross-taxa simple-sequence repeat (SSR) amplification between *Arabidopsis thaliana* L. and crop brassicas," *Theor. Appl. Genet.*, 96:272-281 (1998).
Xu et al., "Methods of plant breeding in the genome era," *Genetics Research*, 92(5-6):423-441 (2010).
Bernacchi et al., "An Interspecific Backcross of *Lycopersicon esculentum* X *L. hirsutum*: Linkage Analysis and a QTL Study of Sexual Compatibility Factors and Floral Traits," *Genetics* 147:861-877 (1997).

TOMATO PLANTS THAT EXHIBIT RESISTANCE TO *BOTRYTIS CINEREA*

RELATED APPLICATION INFORMATION

This application is a continuation of U.S. application Ser. No. 12/816,898, filed Jun. 16, 2010, now U.S. Pat. No. 8,895,803, which is a divisional of U.S. application Ser. No. 10/278,360, filed Oct. 23, 2002, now U.S. Pat. No. 7,799, 976, issued on Sep. 21, 2010, which is a continuation-in-part application of U.S. application Ser. No. 10/131,156, filed Apr. 24, 2002, now abandoned, which claims benefit of U.S. Provisional Application No. 60/286,296, filed Apr. 25, 2001, each of which are herein incorporated by reference in their entirety.

FIELD OF THE INVENTION

The present invention relates to plant breeding and molecular biology. More specifically, the present invention relates to tomato plants that exhibit resistance to *Botrytis cinerea* and methods for developing new inbred, hybrid, apomictic and genetically engineered tomato plants that possess resistance to *Botrytis cinerea* and have commercially desirable characteristics.

BACKGROUND OF THE INVENTION

The plant disease gray mold ("*Botrytis*"), is caused by the fungus *Botrytis cinerea*. This disease is commonly found on the stem, leaves and fruit of tomatoes. While *Botrytis* can be found in both greenhouse and field grown tomatoes, it is a more prevalent problem with greenhouse grown tomatoes. Moisture is of prime importance for *Botrytis* infection. The air must have a relative humidity of above 90% for germination of the pathogen (See, Sherf, A. F., et al., *Vegetable Diseases and Their Control*, John Wiley & Sons (1986), pgs. 645-647). Those areas in which fogs and heavy dews persist are more ideal for the development of the pathogen than areas where heavy rains are common. Id. The optimum temperature for growth of *Botrytis* is between 68° F. and 76° F. Normally, infection is rare above 77° F., although stored infected fruit can rot at temperatures as low as 32° F.

The older, senescent tissues of a tomato plant are usually more susceptible to attack by *Botrytis* than the younger tissues. Typically, the disease is associated with mature plants that have a dense canopy. Leaf lesions develop as light brown or gray, circular spots and may grow to cover the whole leaflet (See, Disease and Pests of Vegetable Crops in Canada, An Illustrated Compendium, Edited by Howard, R., et al., *The Canadian Phytopathological Society, Entomological Society of Canada* (1994)). Affected leaves become covered with conidiophores and conidia, and subsequently collapse and wither. Id. The fungus will grow from diseased leaves into the stem and produce dry, light brown lesions a few millimeters to several centimeters in length. Id. Lesions also form at deleafing scars on the stem. Id. The stem lesions may also be covered with a gray mold. Id. In severe cases, infection girdles the stem and kills the plant.

On green tomato fruit, a "ghost spot" typically appears and is the most common symptom of *Botrytis*. This "ghost spot" is typically tiny brown, often raised, necrotic spot that is surrounded by a pale halo. Id. Typically, once the fruit reaches a certain size, specifically, about 2.5 cm in diameter, the surface becomes smooth and shiny and tends to resist infection. Id. However, it is notable that the fruit can also become infected through flower parts stuck to the surface, particularly at the calyx end, which results in an irregular, brown lesion in the area of the flowering parts.

Unfortunately, the hereinbefore described "ghost spotting" can also occur on ripe fruit. Additionally, mature fruit can also be affected by a rot that starts at the calyx end. Id. Fruit can become water-soaked and soft at the point of infection. Id. The spots are irregular, up to about 3 cm in diameter and light brown to gray. Id. Rotting fruit will eventually fall from the plant.

In addition to tomato, *Botrytis* also affects a wide range of other vegetable crops such as asparagus and lettuce. The disease can be present on perennial plants in any geographical area and sporulation occurs when conditions become optimal (See, *Compendium of Tomato Diseases*, edited by Jones, et al.; APS Press (1991)). Conidia are easily windborn and can be blown from field to field. Id. Moreover, the pathogen can survive from season to season in the form of sclerotia, which develops on the woody tissues of tomato plants. Id. Also, *Botrytis* is a very efficient saprophyte, and organic matter in the soil can harbor it. Id. The fungus grows from the sclerotia or organic matter in the soil and can infect leaves lying on the ground. Id.

In order to discourage the development of *Botrytis* in greenhouse grown tomatoes, the temperature and relative humidity of the greenhouse should be closely regulated. Typically, temperatures higher than 70° F. and a humidity lower than 90% discourage *Botrytis* development. Additionally, at all times, some ventilation or forced air should be employed in the greenhouse as well. The use of drip irrigation or surface water is important to keep the leaves dry and to discourage the development of the pathogen.

For field grown plants, good drainage and weed control should be employed in order to minimize the amount of time that the plants are wet. Moreover, the nutrient levels of the plants should be kept high. It has been found that field grown tomatoes seem to have less infection and loss where nutrient levels, especially nitrogen, are kept high (See, Sherf, A. F., et al., *Vegetable Diseases and Their Control*, John Wiley & Sons (1986), pgs. 645-647).

Fungicides can also be used to control *Botrytis* in both greenhouse and field grown tomatoes. Examples of some fungicides that can be used include chlorothalonil (Exotherm Termil), that can be applied weekly and Dowicide A or DCNA (Botyan), either of which can be applied to tomato fruit post-harvest.

Presently, there are no commercially available tomato varieties that exhibit resistance to infection by *Botrytis*. Thereupon, there is presently a need in the art for new tomato varieties that possess resistance to *Botrytis* and which further exhibit desirable commercial characteristics.

SUMMARY OF THE INVENTION

In one embodiment, the present invention relates to a method of producing a *Botrytis* resistant tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting seed from the cross in step b and growing said seed into plants; (d) selfing the plants of step c; (e) planting seed obtained from the selfing in step d and growing into plants; (f) isolating genetic material from the plants in step e and performing marker assisted selection with one or more molecular markers from chromosome 10 associated with at least one region on chromosome 10 that is linked to at least one gene that encodes for *Botrytis* resistance; and (g) identifying those plants that contain DNA introgressed from the donor plant, where said introgressed DNA contains regions from chromosome 10 linked to at least one gene that encode for *Botrytis* resistance. Preferably, the recipient tomato plant used in said method is *Lycopersicon esculentum*.

In yet another embodiment, the present invention relates to a method of producing a *Botrytis* resistant tomato plant pursuant to the above-described method.

In yet another embodiment, the present invention relates to a method of producing a *Botrytis* resistant inbred tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanumlycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) selfing the plants obtained in step c; (e) planting seed obtained from the cross in step d and growing into plants; (f) isolating genetic material from the plants of step e and performing marker assisted selection with one or more molecular markers from chromosome 10 associated with at least one region on chromosome 10 that is linked to at least one gene that encodes for *Botrytis* resistance; (g) identifying those plants containing DNA introgressed from said donor plant, wherein said introgressed DNA contains regions from chromosome 10, linked to at least one gene that encode for *Botrytis* resistance; (h) selfing the plants identified in step g; (i) planting seed obtained from the selfing in step h and growing into plants; (j) identifying plants from step i that exhibit *Botrytis* resistance and possess commercially desirable characteristics; and (k) repeating steps h-j until an inbred tomato plant is produced which exhibits *Botrytis* resistance and possesses commercially desirable characteristics.

In yet a further embodiment, the present invention relates to a second method of producing a *Botrytis* resistant inbred tomato plant. The method involves the steps of: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) crossing the plants obtained in step c with the recipient tomato plant of step b; (e) planting seed obtained from the crossing in step d and growing into plants; (f) isolating genetic material from the plants of step e and performing marker assisted selection with one or more molecular markers from chromosome 10 associated with at least one region on chromosome 10 that is linked to at least one gene that encodes for *Botrytis* resistance; (g) identifying those plants containing DNA introgressed from said donor plant, wherein said introgressed DNA contains regions from chromosome 10 linked to at least one gene that encode for *Botrytis* resistance; (h) crossing the plants identified in step g with the recipient tomato plant of step b; (i) planting seed obtained from the cross in step h and growing into plants; (j) identifying plants from step i that exhibit *Botrytis* resistance and possess commerically desirable characteristics; and (k) repeating steps h-j until an inbred tomato plant is produced which exhibits *Botrytis* resistance and possesses commercially desirable characteristics.

In yet another embodiment, the present invention relates to a *Botrytis* resistant inbred tomato plant produced by either one of the above-described methods.

In yet another embodiment, the present invention relates to a hybrid tomato plant that exhibits resistance to *Botrytis*. Such a hybrid tomato plant can be produced by crossing an inbred tomato plant produced by one of the above-described methods with an inbred tomato plant that exhibits commercially desirable characteristics.

In yet another embodiment, the present invention relates to a method of producing a *Botrytis* resistant tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting seed from the cross in step b and growing said seed into plants; (d) selfing the plants of step c; (e) planting seed obtained from the selfing in step d and growing into plants; (f) identifying those plants that are resistant to *Botrytis* using a pathology screen. Preferably, the recipient tomato plant used in said method is *Lyopersicon esculentum* and the donor plant contains one or more regions on chromosome 10 linked to at least one gene that encodes for *Botrytis* resistance.

In yet another embodiment, the present invention relates to a method of producing a *Botrytis* resistant tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting seed from the cross in step b and growing said seed into plants; (d) selfing the plants of step c; (e) planting seed obtained from the selfing in step d and growing into plants; (f) inoculating the plants or part of the plants (such as leaves (detached or attached), stems, etc.) grown in step e with *Botrytis*; and (g) identifying those plants inoculated in step f that are resistant to *Botrytis*. Preferably, the recipient tomato plant used in said method is *Lyopersicon esculentum* and the donor plant contains one or more regions on chromosome 10 linked to at least one gene that encodes for *Botrytis* resistance.

In yet another embodiment, the present invention relates to a method of producing a *Botrytis* resistant tomato plant pursuant to the above-described methods.

In yet another embodiment, the present invention relates to a method of producing a *Botrytis* resistant inbred tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) selfing the plants obtained in step c; (e) planting seed obtained from the cross in step d and growing into plants; (f) identifying those plants that are resistant to *Botrytis* using a pathology screen; (g) selfing the plants identified in step f; (h) planting seed obtained from the selfing in step i and growing into plants; (i) identifying plants from step h that exhibit *Botrytis* resistance and possess commercially desirable characteristics; and (j) repeating steps h-i until an inbred tomato plant is produced which exhibits *Botrytis* resistance and possesses commercially desirable characteristics.

In yet a further embodiment, the present invention relates to a second method of producing a *Botrytis* resistant inbred tomato plant. The method involves the steps of: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) crossing the plants obtained in step c with the recipient tomato plant of step b; (e) planting seed obtained from the crossing in step d and growing into plants; (f) identifying those plants that are resistant to *Botrytis* using a pathology screen; (g) crossing the plants identified in step f with the recipient tomato plant of step b; (h) planting seed obtained from the cross in step g and growing into plants; (i) identifying plants from step h that exhibit *Botrytis* resistance and possess commerically desirable characteristics; and (j) repeating steps g-i until an inbred tomato plant is produced which exhibits *Botrytis* resistance and possesses commercially desirable characteristics.

In yet a further embodiment, the present invention relates to a third method of producing a *Botrytis* resistant inbred tomato plant. The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanumlycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) selfing the plants obtained in step c; (e) planting seed obtained from the cross in step d and growing into plants; (f) inoculating the plants or parts of the plants grown in step e with *Botrytis*; (g) identifying those plants inoculated in step f that are resistant to *Botrytis*; (h) selfing the plants identified in step g; (i) planting seed obtained from the selfing in step h and growing into plants; (j) identifying plants from step i that exhibit *Botrytis* resistance and possess commercially desirable characteristics; and (k) repeating steps h-j until an inbred tomato plant is produced which exhibits *Botrytis* resistance and possesses commercially desirable characteristics.

In yet a further embodiment, the present invention relates to a fourth method of producing a *Botrytis* resistant inbred tomato plant. The method involves the steps of: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) crossing the plants obtained in step c with the recipient tomato plant of step b; (e) planting seed obtained from the crossing in step d and growing into plants; (f) inoculating the plants or parts of the plants grown in step e with *Botrytis*; (g) identifying those plants inoculated in step f that are resistant to *Botrytis*; (h) crossing the plants identified in step g with the recipient tomato plant of step b; (i) planting seed obtained from the cross in step h and growing into plants; (j) identifying plants from step i that exhibit *Botrytis* resistance and possess commercially desirable characteristics; and (k) repeating steps h-j until an inbred tomato plant is produced which exhibits *Botrytis* resistance and possesses commercially desirable characteristics.

The method involves at least the following steps: (a) identifying a *Botrytis* resistant donor plant selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) selfing the plants obtained in step c; (e) planting seed obtained from the cross in step d and growing into plants; (f) inoculating the plants or parts of the plants grown in step e with *Botrytis*; (g) identifying those plants inoculated in step f that are resistant to *Botrytis*; (h) selfing the plants identified in step g; (i) planting seed obtained from the selfing in step h and growing into plants; (j) identifying plants from step i that exhibit *Botrytis* resistance and possess commercially desirable characteristics; and (k) repeating steps h-j until an inbred tomato plant is produced which exhibits *Botrytis* resistance and possesses commercially desirable characteristics.

In yet a further embodiment, the present invention relates to a fourth method of producing a *Botrytis* resistant inbred tomato plant. The method involves the steps of: (a) identifying a *Botrytis* resistant donor plant selected from the group consisting of *Lycopersicon esculentum, Lycopersicon cerasifonne, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides*; (b) crossing the *Botrytis* resistant donor plant with a recipient tomato plant that is non-resistant or has an intermediate level of resistance to *Botrytis* and possesses commercially desirable characteristics; (c) planting the seed obtained from the cross in step b and growing into plants; (d) crossing the plants obtained in step c with the recipient tomato plant of step b; (e) planting seed obtained from the crossing in step d and growing into plants; (f) inoculating the plants or parts of the plants grown in step e with *Botrytis*; (g) identifying those plants inoculated in step f that are resistant to *Botrytis*; (h) crossing the plants identified in step g with the recipient tomato plant of step b; (i) planting seed obtained from the cross in step h and growing into plants; (j) identifying plants from step i that exhibit *Botrytis* resistance and possess commercially desirable characteristics; and (k) repeating steps h-j until an inbred tomato plant is produced which exhibits *Botrytis* resistance and possesses commercially desirable characteristics.

In yet another embodiment, the present invention relates to a *Botrytis* resistant inbred tomato plant produced by either one of the above-described methods.

In yet another embodiment, the present invention relates to a hybrid tomato plant that exhibits resistance to *Botrytis*. Such a hybrid tomato plant can be produced by crossing an inbred tomato plant produced by one of the above-described methods with an inbred tomato plant that exhibits commercially desirable characteristics.

In yet another embodiment, the present invention relates to a *Botrytis* resistant tomato plant that contains within its genome at least one gene from chromosome 10 associated with *Botrytis* resistance. Such a *Botrytis* resistant tomato plant is selected from the group consisting of: *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides.*

BRIEF DESCRIPTION OF THE FIGURES

FIG. 1 is a molecular marker map of chromosome 10 in tomato depicting introgression fragment from *L. hirsutum* LA1777 in line TA 1551 as shown in Monforte and Tanksley in *Genome,* 43:803-813 (2000).

FIG. 2 is a molecular marker map of chromosome 10 showing introgression fragments from *L. hirsutum* LA1777 in lines TA1551 and TA1549.

DETAILED DESCRIPTION OF THE INVENTION

Definitions

The headings provided herein are not limitations of the various aspects or embodiments of the invention that can be had by reference to the specification as a whole. Accordingly, the terms defined immediately below are more fully defined by reference to the specification as a whole.

As used herein, the term "allele(s)" means any of one or more alternative forms of a gene, all of which alleles relate to one trait or characteristic. In a diploid cell or organism, the two alleles of a given gene occupy corresponding loci on a pair of homologous chromosomes.

As used herein, the term "*Botrytis*" means *Botrytis cinerea*, also known as gray mold or gray spot, a disease commonly found on the stem, leaves, flowers and fruit of tomatoes.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals (Rieger, R., A Michaelis and M. M. Green, 1968, *A Glossary of Genetics and Cytogenetics*, Springer-Verlag, N.Y.).

As used herein, the term "inbred" means a substantially homozygous individual or variety.

As used herein, the term "introgressed" means the entry or introduction of a gene from one plant into another. As used herein, the term "introgressing" means entering or introducing a gene from one plant into another.

As used herein, the term "molecular marker" means a restriction fragment length polymorphism, (RFLP), amplified fragment length polymorphism (AFLP), single nucleotide polymorphism (SNP), microsatellite, a sequence characterized amplified repeats (SCAR) or an isozyme marker or combinations of the markers described herein which defines a specific genetic and chromosomal location.

As used herein, the term "plant" includes plant cells, plant protoplasts, plant cell tissue cultures from which tomato plants can be regenerated, plant calli, plant cell clumps, and plant cells that are intact in plants, or parts of plants, such as embryos, pollen, ovules, flowers, leaves, seeds, roots, root tips and the like.

As used herein, the term "population" means a genetically heterogeneous collection of plants sharing a common genetic derivation.

As used herein, the term "Restriction Fragment Length Polymorphism" or "RFLP" means a variation between individuals in DNA fragment sizes cut by specific restriction enzymes. Polymorphic sequences that result in RFLPs are used as markers on both physical maps and genetic linkage maps.

As used herein, the term "tomato" means any variety, cultivar, or population of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* and *Solanum lycopersicoides.*

As used herein, the term "variety" or "cultivar" means a group of similar plants that by structural features and performance can be identified from other varieties within the same species.

DESCRIPTION OF THE INVENTION

In one embodiment, the present invention relates to novel *Botrytis* resistant tomato plants and tomato lines, and improved methods for producing them utilizing the molecular markers and genes described herein in selective breeding techniques. More specifically, the inventors of the present invention have identified certain novel *Botrytis* resistant tomato plants. These tomato plants contain one or more genes that encode for *Botrytis* resistance. Tomato plants that do not contain these genes are susceptible to infection by *Botrytis*. Preferably, one or more of the genes that encode for *Botrytis* resistance is located on chromosome 10.

Figure 2:
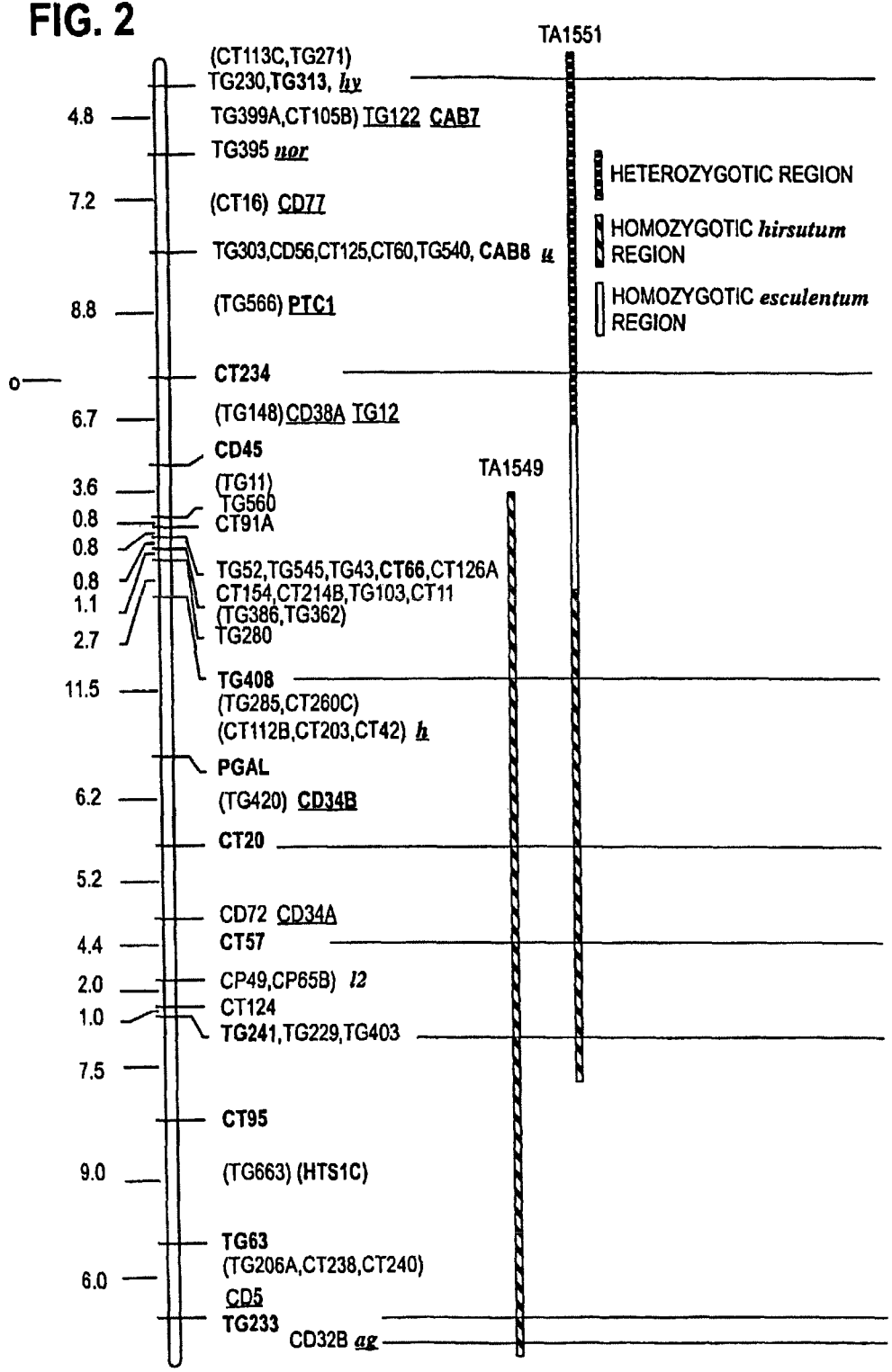

Molecular markers located on chromosome 10 that represent one or more regions on chromosome 10 linked to at least one gene that encodes for *Botrytis* resistance can be identified using marker-assisted selection, the techniques for which are well known in the art. An example of some markers on chromosome 10 believed to be linked to one or more regions on chromosome 10 that are linked to at least one or more genes that encode for *Botrytis* resistance include at least one of, but are not limited to, TG408, CT20, CT57, and TG241 (see FIG. 2).

One source of a *Botrytis* resistant tomato plant that contains the hereinbefore described genes on chromosome 10 is *Lycopersicon hirsutum* accession LA1777. Accession LA1777 is a wild species of tomato that originated in Peru and is publicly available from the C. M. Rick Tomato Genetics Resource Center, Department of Vegetable Crops, University of California, One Shields Avenue, Davis, Calif. 95616. Other related tomato plants that exhibit resistance to *Botrytis* and contain one or more genes that encode for *Botrytis* resistance can now be utilized as the present invention now allows for this material to be identified. More specifically, it is known in the art that the same resistance gene can be present in more than one species, and in fact, more than one Genus (See, Klinger, J., et al., *J. Amer. Soc. Hort. Sci.*, 126(1):56-63 (2001), where the same resistance gene, Vat, which confers resistance to a cotton-melon aphid (*Aphis gossypii* Glover) was discovered in two sources of melon germplasm, Indian accession PI371795 and Korean accession PI 161375; and Grube, R., et al., *Genetics*, 155: 873-887 (2000), where pepper homologues of the cloned R genes Sw-5, N, Pto, Prf, and 12 were found in syntenous positions in other solanaceous genomes and in some cases also mapped to additional positions near phenotypically defined solanaceous R. genes.) Thereupon, other accessions of related tomato species can be examined for *Botrytis* resistance include, but are not limited to, *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon pennellii, Lycopersicon peruvianum, Lycopersicon chilense* and *Solanum lycopersicoides*.

The molecular markers identified as being associated with one or more regions on chromosome 10 that are linked to one or more genes that encode for *Botrytis* resistance can be used to introgress one or more genes that encode for *Botrytis* resistance from a first donor plant into a recipient plant. By way of example, and not of limitation, RFLP screening techniques can be used in said introgression. Tomato plants developed according to the present invention can advantageously derive a majority of their traits from a recipient plant, and derive *Botrytis* resistance from the first donor plant.

According to one aspect of the present invention, genes that encode for *Botrytis* resistance are mapped by identifying molecular markers linked to resistance quantitative trait loci, the mapping utilizing a mix of resistant and susceptible to *Botrytis* inbred tomato plants for phenotypic scoring. Molecular characterization of such lines can be conducted using the techniques described by Monforte and Tanksley in *Genome*, 43:803-813 (2000).

In a second embodiment of the present invention, the present invention relates to methods for producing superior new *Botrytis* resistant tomato plants. In the method of the present invention, one or more genes encoding for *Botrytis* resistance are introgressed from a donor parental plant that is resistant to *Botrytis* into a recipient plant that is either non-resistant or a plant that has intermediate levels of resistance to infection by *Botrytis*. The *Botrytis* resistant tomato plants produced according to the methods of the present invention can be either inbred, hybrid, haploid, apomictic or genetically engineered tomato plants.

The introgression of one or more genes encoding for *Botrytis* resistance into a recipient tomato plant that is non-resistant or possesses intermediate levels of resistance to *Botrytis* can be accomplished using techniques known in the art. For example, one or more genes encoding for *Botrytis* resistance can be introgressed into a recipient tomato plant that is non-resistant or a plant that has intermediate levels of resistance to *Botrytis* using traditional breeding techniques, genetic engineering or protoplast fusion.

As discussed briefly above, traditional breeding techniques can be used to introgress one or more genes encoding for *Botrytis* resistance into a recipient tomato plant that is non-resistant or has an intermediate level of resistance to *Botrytis*. In one method, which is referred to as pedigree breeding, a first tomato plant that exhibits resistance to *Botrytis* and contains one or more genes encoding for *Botrytis* resistance is crossed with a second tomato plant that is non-resistant to *Botrytis* or possesses intermediate levels of resistance to *Botrytis* and that exhibits commercially desirable characteristics, such as, but not limited to, disease resistance, insect resistance, valuable fruit characteristics, etc. The resulting plant population (that are F1 hybrids) is then allowed to self-pollinate and set seeds (F2 seeds). The F2 plants grown from the F2 seeds are then screened for resistance to *Botrytis*. The population can be screened in a number of different ways. First, the population can be screened using a traditional pathology disease screen. Such pathology disease screens are known in the art. Specifically, the individual plants or parts thereof can be challenged in an incubator or greenhouse with *Botrytis* and the resulting resistant or susceptible phenotypes of each plant scored. By way of example, and not of limitation, plants can be screened in a greenhouse as follows.

First, tomato seeds are planted and grown to seedlings (approximate time ~6 weeks) in the greenhouse (hereinafter "GH"). Three (3) repetitions of ten (10) plants each for a total of thirty (30) plants per line are evaluated. The leaves, stems, flowers and fruits can be rated separately using a disease rating scale of 1-5 (1=resistant and 5=susceptible). The plants are inoculated with a conidial suspension (1,000,000 conidia/ml) of *Botrytis* 10 weeks after planting. A second inoculation may be required to enhance the disease development on the stems and fruit.

The leaves can be evaluated for *Botrytis* sporulation and lesion development one week after inoculation using the following disease rating scale (1=resistant and 5=susceptible):

1—No symptoms.

2—Necrosis and sporulation present on 1-2 leaves.

3—Necrosis and sporulation present on 10% of the foliage.

4—Necrosis and sporulation present on 20% of the foliage.

5—Necrosis and sporulation present on greater than 20% of the foliage.

The stems can be evaluated for *Botrytis* sporulation and lesion development 4 weeks after inoculation using the following disease rating scale (1=resistant and 5=susceptible):

1—No symptoms.
2—Limited superficial lesions on the stem.
3—Lesion expanding to 10 mm diameter with limited sporulation.
4—Lesions expanding to 40 mm diameter, depressed with sporulation.
5—Lesions expanding to greater than 40 mm diameter, depressed with sporulation or stems completely girdled.

The flowers can be evaluated for *Botrytis cinerea* disease development and sporulation when at least 3 flower clusters had developed using the following disease rating scale (1=resistant and 5=susceptible):

1—No symptoms.
2—Flower abscission, necrosis and or sporulation on less than 50% of the flowers in one cluster.
3—Flower abscission, necrosis and or sporulation on less than 50% of the flowers in two or more clusters.
4—Flower abscission, necrosis and or sporulation on 50% to 75% of the flowers in two or more clusters.
5—Flower abscission, necrosis and or sporulation on greater than 75% of the flowers in all clusters.

The fruit can be evaluated for *Botrytis* lesion development when 50% of the fruit are at the break stage of development using the following disease rating scale (1=resistant and 5=susceptible):

1—No symptoms.
2—Lesions on the peduncle only.
3—Lesions developing on one fruit only.
4—Lesions developing on up to 4 fruit per plant.
5—Lesions developing on more than 4 fruit per plant.

Second, marker-assisted selection can be performed using one or more of the hereinbefore described molecular markers to identify those hybrid plants that contain one or more of the genes that encode for *Botrytis* resistance. Alternatively, marker-assisted selection can be used to confirm the results obtained from the pathology screen.

F2 hybrid plants exhibiting a *Botrytis* resistant phenotype contain the requisite genes encoding for *Botrytis* resistance, and possess commercially desirable characteristics, are then selected and selfed for a number of generations in order to allow for the tomato plant to become increasingly inbred. This process of continued selfing and selection can be performed for five or more generations. The result of such breeding and selection is the production of lines that are genetically homogenous for the genes associated with *Botrytis* resistance as well as other genes associated with traits of commercial interest.

Alternatively, a new and superior *Botrytis* resistant inbred tomato plant line can be developed using the techniques of recurrent selection and backcrossing. In this method, *Botrytis* resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has an intermediate level of resistance to *Botrytis* and possesses commercially desirable characteristics, such as, but not limited to disease resistance, insect resistance, valuable fruit characteristics, etc. The non-recurrent parent exhibits *Botrytis* resistance and contains one or more genes that encode for *Botrytis* resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. First, the population can be screened using a traditional pathology screen as described previously herein.

Second, marker-assisted selection can be performed using one or more of the hereinbefore described molecular markers to identify those progeny that contain one or more of genes encoding for *Botrytis* resistance. Alternatively, marker-assisted selection can be used to confirm the results obtained from the pathology screen.

Once the appropriate selections are made, the process is repeated. The process of backcrossing to the recurrent parent and selecting for *Botrytis* resistance is repeated for approximately five or more generations. The progeny resulting from this process are heterozygous for one or more genes that encode for *Botrytis* resistance. The last backcross generation is then selfed in order to provide for homozygous pure breeding progeny for *Botrytis* resistance.

The *Botrytis* resistant inbred tomato lines described herein can be used in additional crossings to create *Botrytis* resistant hybrid plants. For example, a first *Botrytis* resistant inbred tomato plant can be crossed with a second inbred tomato plant possessing commercially desirable traits such as, but not limited to, disease resistance, insect resistance, desirable fruit characteristics, etc. This second inbred tomato line may or may not be resistant to *Botrytis*.

The marker-assisted selection used in the hereinbefore described methods can be made, for example, step-wise, whereby the different *Botrytis* resistant genes are selected in more than one generation; or, as an alternative example, simultaneously, whereby all resistance genes are selected in the same generation. Marker-assisted selection for *Botrytis* resistance may be done before, in conjunction with, or after testing and selection for other commercially desirable traits such as disease resistance, insect resistance, desirable fruit characteristics, etc.

In yet another embodiment, the present invention relates to the identification, isolation and purification of one or more genes from tomato that encodes for *Botrytis* resistance. A source of material from which such gene(s) can be isolated from is *Lycopersicon hirsutum* accession LA 1777. Additionally, the present invention further contemplates the insertion of such isolated and purified genes either into tomato or other plants using techniques known in the art in order to provide transgenic plants that exhibit resistance to *Botrytis* infection.

Plant transformation involves the construction of an expression vector that will function in plant cells. In the present invention, such a vector comprises DNA comprising a gene that encodes for *Botrytis* resistance that is under control of or operatively linked to a regulatory element, such as a promoter. The expression vector may contain one or more such operably linked gene/regulatory element combinations, provided that at least one of the genes contained in said combinations encodes for *Botrytis* resistance. The vector(s) may be in the form of a plasmid, and can be used, alone or in combination with other plasmids, to provide transgenic plants that are resistant to *Botrytis*, using transformation methods described below.

Expression vectors can include at least one genetic marker, operably linked to a regulatory element (such as a promoter) that allows transformed cells containing the marker to be either recovered by negative selection (by inhibiting the growth of cells that do not contain the selectable marker gene), or by positive selection (by screening for the product encoded by the genetic marker). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, markerless transformation can be used, the techniques for which are known in the art.

An example of a commonly used selectable marker gene for plant transformation is the neomycin phosphotransferase II (nptII) gene, isolated from transposon Tn5, which when placed under the control of a plant regulatory signal confers resistance to kanamycin (See, Fraley et al., *Proc. Natl. Acad. Sci. U.S.A*, 80:4803 (1983)). Another commonly used selectable marker gene is the hygromycin phosphotransferase gene that confers resistance to the antibiotic hygromycin (See, Vanden Elzen et al., *Plant Mol. Biol.*, 5:299 (1985)). Examples of other selectable markers that can be used include beta-glucuronidase (GUS), beta-galactosidase, luciferase and chloramphenicol acetyltransferase.

Expression vectors must be driven by a nucleotide sequence comprising a regulatory element, such as a promoter. Several types of promoters are well known in the art, as are other regulatory elements that can be used alone or in combination with promoters. As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in certain tissues are referred to as "tissue-specific". A "cell type" specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

An inducible promoter is operably linked to an isolated and purified gene that encodes for *Botrytis* resistance for expression in tomato. With an inducible promoter, the rate of transcription increases in response to an inducing agent. Any inducible promoter can be used in the present invention.

A constitutive promoter can be operably linked to an isolated and purified gene that encodes for *Botrytis* resistance for expression in tomato. Several different constitutive promoters are known in the art and can be used in the present invention. An example of a constitutive promoter that can be used in the present invention includes, but is not limited to, promoters from plant viruses such as the 19S or 35S promoter from CaMV (See, Odell et al., *Nature*, 313:810-812 (1985)).

A tissue-specific promoter is operably linked to an isolated and purified gene that encodes for *Botrytis* resistance for expression in tomato. Plants transformed with an isolated and purified gene that encodes for *Botrytis* resistance operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a leaf-specific and light-induced promoter such as that from cab or rubisco (See, Simpson et al., *EMBO J.*, 4(11):2723-2729 (1985) and Timko et al., *Nature*, 318: 579-582 (1985)).

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thmpson, J. E. Eds. (CRC Press, Inc. Boca Raton, 1993) pages 67-88. In addition, expression vectors and in vitro culture methods for plant cell or tissue transformation and regeneration of plants are available (See, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119)).

One method for introducing an expression vector into a plant is based on the natural transformation system of *Agrobacterium* (See, Horsch et al., Science, 227:1229 (1985)). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (See, Kado, C. I., *Crit. Rev. Plant. Sci.*, 10:1 (1991)). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616, issued Jan. 7, 1997.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., *Part. Sci. Technol.* 5: 27 (1987), Sanford, J. C., *Trends Biotech.*, 6:299 (1988), Klein et al., *Bio/Technology*, 6:559-563 (1988). Sanford J. C., *Physiol Plant*, 79:206 (1990), Klein et al., *Biotechnology*, 10:268 (1992)).

Another method for introducing DNA to plants is via the sonication of target cells (See, Zhang et al., *Bio/Technology*, 9:996 (1991)). Alternatively, liposome or spheroplast fusion have been used to introduce expression vectors into plants (See, Deshayes et al., *EMBO J.*, 4:2731 (1985), Christou et al., *Proc Natl. Acad. Sci. U.S.A*, 84:3962 (1987)). Direct uptake of DNA into protoplasts using $CaCl_2$ precipitation, polyvinyl alcohol or poly-L-ornithine have also been reported (See, Hain et al., *Mol. Gen. Genet.*, 199:161 (1985) and Draper et al., *Plant Cell Physiol.*, 23: 451 (1982)). Electroporation of protoplasts and whole cells and tissues have also been described (Donn et al., In *Abstracts of VIIth International Congress on Plant Cell and Tissue Culture IAPTC*, A2-38, p 53 (1990); D'Halluin et al., Plant cell, 4:1495-1505 (1992) and Spencer et al., *Plant Mol. Biol.*, 24:51-61 (1994)).

Following transformation of tomato target tissues, expression of the above-described selectable marker genes allows for preferential selection of transformed cells, tissues and/or plants, using regeneration and selection methods now well known in the art.

The foregoing methods for transformation could be used for producing transgenic tomato plants or other plant species, such as, but not limited to, vegetables (i.e. asparagus, lettuce, etc.) fruit (i.e. strawberries), or ornamental plants (i.e, African Violet, Begonias, *Bougainvillea*, Cyclamen, Dahlia, Geranium, Chinese Hibiscus, *Impatiens*, Kalanchoe, Ornamental Pepper, Persian Violet, Primrose, Poinsettia, *Verbena, Vinca*, etc.) that contain a foreign (heterologous) gene(s) that encodes for *Botrytis* resistance. Such transgenic plants can then be crossed, with another (non-transformed or transformed) plants, in order to produce a transgenic hybrid of tomato or other plant species that is resistant to *Botrytis* infection. Alternatively, the foreign (heterologous) genes for *Botrytis* resistance in a transgenic tomato or other plant species that has been engineered to contain said foreign (heterologous) gene(s) that encodes for *Botrytis* resistance using the transformation techniques described herein could be moved into another plant using traditional breeding techniques (such as backcrossing), that are well-known in the art. For example, and as previously discussed herein, backcrossing could be used to introgress *Botrytis* resistance from a transgenic *Botrytis* resistant inbred tomato or other plant line containing a foreign (heterologous) gene that encodes for *Botrytis* resistance to a non-resistant tomato plant or other crop that does not contain that gene, or from a transgenic hybrid *Botrytis* resistant tomato plant or other plant containing a foreign gene that encodes for *Botrytis* resistance into a line(s) that does not contain that gene.

In another embodiment, protoplast fusion can be used to create superior new *Botrytis* resistant plants. More specifically, a first protoplast can be obtained from a tomato plant or other plant line that exhibits resistance to infection by *Botrytis* and contains the genes described herein. For example, a protoplast from *Lycopersicon hirsutum* accession LA1777 can be used. A second protoplast can be obtained from a second tomato or other plant variety that contains commercially desirable characteristics, such as, but not limited to disease resistance, insect resistance, valuable fruit characteristics, etc. The protoplasts are then fused using traditional protoplast fusion procedures which are known in the art. For example, the protoplast fusion can be accomplished by employing a polyethylene glycol (PEG) solution to facilitate the fusion of the membranes. Such somatic hybridization may be effected under the conditions disclosed by Sundberg et al. (*Plant Science,* 43:155 (1986), for the production of interspecific hybrids or modifications thereof. However, one skilled in the art would recognize that the protoplast fusion can be accomplished in other ways other than using polyethylene glycol (PEG). For example, the protoplasts can be fused by using electric field-induced fusion techniques as described by Koop et al., "Electric Field-Induced Fusion and Cell Reconstruction—with Preselected Single Protoplasts and Subprotoplasts of Higher Plants" in *Electroporation and Electrofusion in Cell Biology*, Neuman et al., editors, pgs. 355-265 (1989). Additionally, protoplast fusion can be accomplished with dextran and polyvinyl alcohol as described by Hauptmann et al., "Carrot×Tobacco Somatic Cell Hybrids Selected by Amino Acid Analog Resistance Complementation", $6^{th}$ International Protoplast Symposium, Basel, Switzerland, Aug. 12-16, 1983.

In another embodiment, the present invention provides methods for determining the presence or absence of *Botrytis* resistance in a tomato plant, or alternatively in a tomato seed. These methods comprise analyzing DNA from a plant or a seed for the presence of one or more molecular markers that are associated with at least one region on a chromosome that is linked to at least one gene that encodes for *Botrytis* resistance. More specifically, the molecular markers are preferably from chromosome 10 and are used to identify one or more regions on chromosome 10 that are linked to at least one gene that encodes for *Botrytis* resistance. An example of such markers include, but are not limited to at least one of the following: TG408, CT20, CT57 and TG241 on chromosome 10. According to this method, the analyzing comprises analyzing the tomato plants or seed by RFLP analysis.

In another embodiment, the present invention relates to seed, a plant and/or a plant line which is produced pursuant to the hereinbefore described methods. More specifically, the present invention relates to a *Botrytis* resistant tomato plant, or alternatively a plant line, such as, but not limited to vegetables (i.e. asparagus, lettuce, etc.) fruit (i.e. strawberries), or ornamental plants (i.e, African Violet, Begonias, *Bougainvillea*, Cyclamen, Dahlia, Geranium, Chinese Hibiscus, *Impatiens*, Kalanchoe, Ornamental Pepper, Persian Violet, Primrose, Poinsettia, *Verbena, Vinca*, etc.) derived from selective breeding, which comprises first genomic DNA from a first plant line, the first genomic DNA conferring *Botrytis* resistance to the plant line; and second genomic DNA from a second plant line, the second genomic DNA conferring other desired traits to the plant line. According to this aspect of the invention, in tomato, the first amount of genomic DNA comprises molecular markers from chromosome 10 that are associated with at least one region on chromosome 10 that is linked to at least one gene that encodes for *Botrytis* resistance. More specifically, in tomato, the molecular markers, including at least one, but are not limited to, TG408, CT20, CT57 and TG241 on chromosome 10.

By way of example, and not of limitation, Examples of the present invention will now be given.

Example 1

Resistance to *Botrytis* in *Lycopersicon hirsutum*×*L. esculentum* Backcross Recombinant Inbred Lines Seeds of the following *Lycopersicon hirsutum*×*L. esculentum* backcross recombinant inbred lines (hereinafter "RIL") were sent to Latina, Italy for resistance evaluation under greenhouse conditions in the year 2000. Seeds were planted into soil in transplant trays and grown in the greenhouse between 20° C. and 24° C. for approximately 6 weeks. Specifically, the seeds were from the following lines: LA1777, TA1551, TA1330, TA1276, TA1105, TA1277, TA1541, TA1324, TA517, TA1266, TA1544, TA1316, TA1539, TA1121, TA1112, TA1545, TA1562, TA1258, TA1304, TA1280, TA1548, TA1127, TA1535, TA1540 and E6203. All the lines are publicly available from the C.M. Rick Tomato Genetics Resource Center, Department of Vegetable Crops, University of California, One Shields Avenue, Davis, Calif. 95616. These lines have been described by Monforte and Tanksley in *Genome,* 43:803-813 (2000).

Seedlings were transplanted to the greenhouse (hereinafter "GH") approximately 6 weeks after planting. Three repetitions of 10 plants each for a total of 30 plants per line were evaluated. The leaves and stems were rated separately using a disease rating scale of 1-5 (1=resistant and 5=susceptible).

The plants were inoculated with a conidial suspension (1,000,000 conidia/ml) of *Botrytis cinerea* 4 weeks after transplanting. A second inoculation was made five weeks after the first inoculation to enhance the disease development on the stems.

The leaves were evaluated for *Botrytis cinerea* sporulation and lesion development one week after inoculation using the following disease rating scale (1=resistant and 5=susceptible):

1—No symptoms.
2—Necrosis and sporulation present on 1-2 leaves.
3—Necrosis and sporulation present on 10% of the foliage.
4—Necrosis and sporulation present on 20% of the foliage.
5—Necrosis and sporulation present on greater than 20% of the foliage.

The stems were evaluated for *Botrytis cinerea* sporulation and lesion development 4 weeks after inoculation using the following disease rating scale (1=resistant and 5=susceptible):

1—No symptoms.
2—Limited superficial lesions on the stem.
3—Lesion expanding to 10 mm diameter with limited sporulation.
4—Lesions expanding to 40 mm diameter, depressed with sporulation.
5—Lesions expanding to greater than 40 mm diameter, depressed with sporulation or stems completely girdled.

Tables 1 and 2 below show the disease ratings of the leaves and stems from *Lycopersicon esculentum* backcross recombinant inbred lines containing various introgression fragments from *L. hirsutum* against infection from *Botrytis cinerea*.

TABLE 1

Average leaf disease rating of LA 1777 introgression lines screened for resistance to the fungal disease gray mold under greenhouse conditions in June 2000.

| RIL[1] | Avg Leaf Rating[2] | N[3] | p value[4] |
|---|---|---|---|
| TA1551 | 2.8 | 30 | 0.065 |
| TA1330 | 3.4 | 30 | 0.120 |
| TA1105 | 3.5 | 30 | 0.170 |
| TA1544 | 3.6 | 28 | 0.093 |
| TA1316 | 3.6 | 27 | 0.480 |
| TA1539 | 3.6 | 26 | 0.090 |
| TA1277 | 3.6 | 30 | 0.396 |
| TA1121 | 3.8 | 20 | 0.632 |
| TA1112 | 3.8 | 30 | 0.439 |
| TA1545 | 4.0 | 27 | 0.955 |
| TA1562 | 4.1 | 29 | 0.806 |
| TA1258 | 4.1 | 30 | 0.855 |
| TA1304 | 4.1 | 26 | 0.824 |
| TA1541 | 4.1 | 30 | 0.657 |
| TA1324 | 4.1 | 30 | 0.686 |
| TA1280 | 4.1 | 22 | 0.553 |
| TA1548 | 4.2 | 30 | 0.521 |
| TA1127 | 4.2 | 30 | 0.486 |
| TA1535 | 4.2 | 21 | 0.270 |
| TA517 | 4.3 | 29 | 0.543 |
| TA1276 | 4.4 | 29 | 0.241 |
| TA1266 | 4.5 | 29 | 0.287 |
| TA1540 | 5.0 | 16 | 0.009 |
| LA1777[5] | na | 30 | na |
| E6203 | 4.1 | 35 | |

[1]*Lycopersicon hirsutum* (LA 1777) RIL in *L. esculentum* (E6203).
[2]Average disease rating of RIL stems (1 = resistant; 5 = susceptible).
[3]Number of plants evaluated.
[4]RIL is significantly different from E6203 if p is less than 0.05.
[5]Leaves were not rated due to natural senescence of the older leaves in *L. hirsutum* at the time disease ratings were taken.

TABLE 2

Average stem disease rating of LA 1777 introgression lines screened for resistance to the fungal disease gray mold under greenhouse conditions in June 2000.

| RIL[1] | Avg Stem rating[2] | N[3] | p value[4] |
|---|---|---|---|
| LA1777 | 1.00 | 30 | 0.003 |
| TA1551 | 1.80 | 30 | 0.009 |
| TA1276 | 2.27 | 30 | 0.175 |
| TA1105 | 2.43 | 30 | 0.160 |
| TA1277 | 2.63 | 30 | 0.277 |
| TA1541 | 2.70 | 30 | 0.063 |
| TA1548 | 2.70 | 30 | 0.063 |
| TA1112 | 2.80 | 30 | 0.560 |
| TA1324 | 2.83 | 30 | 0.338 |
| TA517 | 3.03 | 29 | 0.616 |
| TA1127 | 3.20 | 30 | 0.549 |
| TA1544 | 3.21 | 28 | 0.177 |
| TA1304 | 3.22 | 27 | 0.181 |
| TA1330 | 3.29 | 28 | 0.383 |
| TA1266 | 3.29 | 28 | 0.728 |
| TA1562 | 3.31 | 29 | 0.904 |
| TA1539 | 3.37 | 30 | 0.934 |
| TA1535 | 3.40 | 20 | 0.440 |
| TA1280 | 3.48 | 23 | 0.920 |
| TA1540 | 3.56 | 16 | 0.585 |
| TA1258 | 3.57 | 30 | 0.765 |
| TA1316 | 3.59 | 27 | 0.449 |
| TA1121 | 3.65 | 20 | 0.761 |
| TA1545 | 3.79 | 28 | 0.005 |
| E6203 | 3.37 | 35 | |

[1]*Lycopersicon hirsutum* (LA 1777) RIL in *L. esculentum* (E6203).
[2]Average disease rating of RIL stems (1 = resistant; 5 = susceptible).
[3]Number of plants evaluated.
[4]RIL is significantly different from E6203 if p is less than 0.05.

The level of resistance observed in line TA1551 for the stem rating (p=0.009) demonstrate that it is significantly more resistant than its parent line E6203. In addition, the level of resistance observed in the leaf rating, although not significant at p=0.05, is greater than that observed in the parent line E6203. (see Tables 1 and 2).

Line TA1551 contains an introgression segment from chromosome 10 of *L. hirsutum* as described by Monforte and Tanksley in *Genome*, 43:803-813 (2000) (see FIG. 1).

Example 2

Resistance to *Botrytis* in *Lycopersicon hirsutum*×*L. esculentum* Backcross Recombinant Inbred Lines To further evaluate the resistance observed in line TA1551 in the greenhouse screen in 2000 (see example 1) seeds of the following *Lycopersicon hirsutum*×*L. esculentum* backcross recombinant inbred lines were sent to Latina, Italy for resistance evaluation under greenhouse conditions in 2001. Seeds were planted into soil in transplant trays and grown in the greenhouse between 20° C. and 24° C. for approximately 6 weeks. Specifically, the seeds were from the following lines: LA1777, TA1551, TA1551-F1, TA1339, E6203 and Max. Except for TA1551-F1 and Max, the other lines are publicly available from the C.M. Rick Tomato Genetics Resource Center, Department of Vegetable Crops, University of California, One Shields Avenue, Davis, Calif. 95616. The recombinant backcross inbred lines TA1551 and TA1339 are described by Monforte and Tanksley in *Genome*, 43:803-813 (2000).

Seedlings were transplanted to the greenhouse approximately 6 weeks after planting. Three repetitions of 10 plants each for a total of 30 plants per line were evaluated. The leaves, and stems, flowers and fruits were rated separately using a disease rating scale of 1-5 (1=resistant and 5=susceptible).

The plants were inoculated with a conidial suspension (1,000,000 conidia/ml) of *Botrytis cinerea* four (4) weeks after transplanting. A second inoculation was made five weeks after the first inoculation to enhance the disease development on the stems and fruit.

The leaves were evaluated for *Botrytis cinerea* sporulation and lesion development one week after inoculation using the following disease rating scale (1=resistant and 5=susceptible):

1—No symptoms.
2—Necrosis and sporulation present on 1-2 leaves.
3—Necrosis and sporulation present on 10% of the foliage.
4—Necrosis and sporulation present on 20% of the foliage.
5—Necrosis and sporulation present on greater than 20% of the foliage.

The stems were evaluated for *Botrytis cinerea* sporulation and lesion development 4 weeks after inoculation using the following disease rating scale (1=resistant and 5=susceptible):

1—No symptoms.
2—Limited superficial lesions on the stem.
3—Lesion expanding to 10 mm diameter with limited sporulation.
4—Lesions expanding to 40 mm diameter, depressed with sporulation.
5—Lesions expanding to greater than 40 mm diameter, depressed with sporulation or stems completely girdled.

The flowers were evaluated for *Botrytis cinerea* disease development and sporulation when at least 3 flower clusters had developed using the following disease rating scale (1=resistant and 5=susceptible):

1—No symptoms.
2—Flower abscission, necrosis and or sporulation on less than 50% of the flowers in one cluster.
3—Flower abscission, necrosis and or sporulation on less than 50% of the flowers in two or more clusters.
4—Flower abscission, necrosis and or sporulation on 50% to 75% of the flowers in two or more clusters.
5—Flower abscission, necrosis and or sporulation on greater than 75% of the flowers in all clusters.

The fruit were evaluated for *Botrytis cinerea* lesion development when 50% of the fruit were at the break stage of development using the following disease rating scale (1=resistant and 5=susceptible):

1—No symptoms.
2—Lesions on the peduncle only.
3—Lesions developing on one fruit only.
4—Lesions developing on up to 4 fruit per plant.
5—Lesions developing on more than 4 fruit per plant.

Table 3 below shows the disease ratings of the leaves, stems, flowers and fruit from *Lycopersicon esculentum* backcross recombinant inbred lines containing an introgression fragment from *L. hirsutum* against infection from *Botrytis cinerea*.

TABLE 3

Average leaf, stem, flower and fruit disease score of tomato lines screened for resistance to the fungal disease gray mold under greenhouse conditions in June 2001.

| Line | $N^1$ | Average Leaf rating$^2$ | p-Value$^3$ | Average Stem$^2$ rating | p-Value$^3$ | Average Flower rating | p-Value$^3$ | Average Fruit Rating$^2$ | p-Value$^3$ |
|---|---|---|---|---|---|---|---|---|---|
| LA1777 | 30 | $NA^4$ | na | 1.0 | 0.00 | 1.0 | 0.01 | 1.0 | 0.01 |
| TA1551 | 25 | 2.2 | 0.01 | 1.0 | 0.00 | 1.0 | 0.01 | 1.0 | 0.01 |
| TA1551 F1 | 15 | 2.4 | 0.08 | 1.8 | 0.38 | 1.1 | 0.02 | 1.0 | 0.04 |
| TA1339 | 30 | 3.0 | 0.07 | 2.1 | 0.06 | 1.8 | 0.13 | 2.5 | 0.01 |
| MAX | 21 | 5.0 | 0.01 | 3.0 | 0.48 | 1.9 | 0.41 | 3.8 | 0.02 |
| E6203 | 29 | 3.5 | | 2.7 | | 2.1 | | 2.0 | |

[1] Number of plants evaluated.
[2] Average disease rating for leaf, stem, flower and fruit (1 = resistant; 5 = susceptible).
[3] Lines have significantly less disease compared to E6203 if p is less than 0.05.
[4] Leaves were not rated due to natural senescence of the older leaves in *L. hirsutum* at the time disease ratings were taken.

The levels of resistance observed for line TA1551 for the leaves (p=0.01), stem (p=0.00), flower (p=0.01) and fruit (p=0.01) demonstrate that it is significantly more resistant than its parent line E6203 (see Table 3).

In addition, line TA1339 showed no significant difference at p=0.05 in disease development as compared to the susceptible E6203 for the average leaf (p=0.07), stem (p=0.06) and flower (p=0.13) score. Also, it showed significantly more disease development on the fruit than the susceptible check E6203, indicating that it does not contribute to disease resistance.

Line TA1551 and TA1339 contain introgression segments from chromosome 10 of *L. hirsutum* as described by Monforte and Tanksley in *Genome*, 43:803-813 (2000) (see FIG. 1).

Example 3

Resistance to *Botrytis* in *Lycopersicon hirsutum*×*L. esculentum* Backcross Recombinant Inbred Lines To obtain a more detailed understanding of the region on chromosome 10 that is responsible for resistance, additional *Lycopersicon hirsutum*×*L. esculentum* backcross recombinant inbred lines containing chromosome 10 introgressions were evaluated along with lines that did not contain chromosome 10 introgressions in the greenhouse screen at Latina Italy in 2002. Seeds of the following *Lycopersicon hirsutum*×*L. esculentum* RIL's were sent to Latina, Italy for resistance evaluation under greenhouse conditions. Seeds were planted into soil in transplant trays and grown in the greenhouse between 20° C. and 24° C. for approximately 6 weeks. Specifically, the seeds were from the following lines: TA1331, TA1337, TA1339, TA1546, TA1549, TA1551, TA1552, TA1555, TA1559, TA1564, TA1630, TA1654, LA1777, and E6203. These lines are publicly available from the C.M. Rick Tomato Genetics Resource Center, Department of Vegetable Crops, University of California, One Shields Avenue, Davis, Calif. 95616. The recombinant backcross inbred lines are described by Monforte and Tanksley in *Genome,* 43:803-813 (2000).

Seedlings were transplanted to the greenhouse approximately 6 weeks after planting. Three repetitions of approximately 20 plants each for a total of 60 plants per line were evaluated. The leaves, stems, and flowers were rated separately using a disease rating scale of 1-5 (1=resistant and 5=susceptible).

The plants were inoculated with a conidial suspension (1,000,000 conidia/ml) of *Botrytis cinerea* four (4) weeks after transplanting. A second inoculation was made five weeks after the first inoculation to enhance the disease development on the stems.

The leaves were evaluated for *Botrytis cinerea* sporulation and lesion development one week after inoculation using the following disease rating scale (1=resistant and 5=susceptible):

1—No symptoms.
2—Necrosis and sporulation present on 1-2 leaves.
3—Necrosis and sporulation present on 10% of the foliage.
4—Necrosis and sporulation present on 20% of the foliage.
5—Necrosis and sporulation present on greater than 20% of the foliage.

The stems were evaluated for *Botrytis cinerea* sporulation and lesion development 4 weeks after inoculation using the following disease rating scale (1=resistant and 5=susceptible):

1—No symptoms.
2—Limited superficial lesions on the stem.
3—Lesion expanding to 10 mm diameter with limited sporulation.
4—Lesions expanding to 40 mm diameter, depressed with sporulation.
5—Lesions expanding to greater than 40 mm diameter, depressed with sporulation or stems completely girdled.

The flowers were evaluated for *Botrytis cinerea* disease development and sporulation when at least 3 flower clusters had developed using the following disease rating scale (1=resistant and 5=susceptible):

1—No symptoms.
2—Flower abscission, necrosis and or sporulation on less than 50% of the flowers in one cluster.
3—Flower abscission, necrosis and or sporulation on less than 50% of the flowers in two or more clusters.
4—Flower abscission, necrosis and or sporulation on 50% to 75% of the flowers in two or more clusters.
5—Flower abscission, necrosis and or sporulation on greater than 75% of the flowers in all clusters.

Table 4 below shows the disease ratings of the leaves, stems, and flowers from *Lycopersicon esculentum* backcross recombinant inbred lines containing an introgression fragment from *L. hirsutum* against infection from *Botrytis cinerea.*

TABLE 4

Average leaf, stem, and flower disease score of tomato lines screened for resistance to the fungal disease gray mold under greenhouse conditions in June 2002.

| Line | N[1] | Avg Leaf rating[2] | p value[3] | Avg Stem rating[2] | p value[3] | Average Flower rating[2] | p value[3] |
|---|---|---|---|---|---|---|---|
| LA1777 | 21 | 1.42 | 0.053 | 1.00 | 0.009 | 1.00 | 0.020 |
| TA1551 | 42 | 1.48 | 0.006 | 1.25 | 0.002 | 1.29 | 0.038 |
| TA1549 | 56 | 1.21 | 0.003 | 1.34 | 0.016 | 1.05 | 0.024 |
| TA1552 | 60 | 2.33 | 0.107 | 2.17 | 0.190 | 2.55 | 0.075 |
| TA1559 | 60 | 2.25 | 0.236 | 2.52 | 0.409 | 2.62 | 0.215 |
| TA1564 | 59 | 2.93 | 0.835 | 2.56 | 0.134 | 3.12 | 0.350 |
| TA1546 | 58 | 2.69 | 0.098 | 2.72 | 0.665 | 2.55 | 0.064 |
| TA1337 | 59 | 2.68 | 0.160 | 2.75 | 0.323 | 2.20 | 0.174 |
| TA1339 | 55 | 2.71 | 0.085 | 2.75 | 0.406 | 3.62 | 0.671 |
| TA1331 | 60 | 2.80 | 0.513 | 2.83 | 0.553 | 2.77 | 0.145 |
| TA1555 | 58 | 2.76 | 0.322 | 2.85 | 0.604 | 2.57 | 0.244 |
| TA1630 | 58 | 2.97 | 0.878 | 2.88 | 0.816 | 3.57 | 0.559 |
| TA1654 | 59 | 2.92 | 0.826 | 2.90 | 0.942 | 3.34 | 0.491 |
| E6203 | 59 | 3.02 | | 2.95 | | 3.73 | |

[1]Number of plants evaluated.
[2]Average disease rating for leaf, stem, flower and fruit (1 = resistant; 5 = susceptible).
[3]Lines have significantly less disease compared to E6203 if p is less than 0.05.

The levels of resistance observed based on the disease ratings for line TA1551 for the leaves (p=0.006), stem (p=0.002), and flower (p=0.038) demonstrate that it is significantly more resistant than its parent line E6203 (see Table 4).

In addition, the levels of resistance observed based on the disease ratings for line TA1549 for the leaves (p=0.003), stem (p=0.016), and flower (p=0.024) demonstrate that it is significantly more resistant than its parent line E6203 (see Table 4).

Lines TA1551 and TA1549 contain introgression segments from chromosome 10 of *L. hirsutum* as described by Monforte and Tanksley in *Genome,* 43:803-813 (2000) (see FIG. 1).

Additional marker analysis of RIL TA1551 revealed that the introgression segment from LA1777 was heterozygous in the region containing markers TG313 and CT234. In addition, a double crossover was detected which resulted in a homozygotic *L. esculentum* genotype in the region containing marker CD45. Further, the region of TA1551 containing markers TG408, CT20, CT57 and TG241 was found to be homozygous for *L. hirsutum* (see FIG. 2). Detailed marker analysis for RIL TA1549 revealed that the introgression segment from LA 1777 was homozygous in the region containing markers TG408, CT20, CD34, TG241, CT95, TG63 and TG233 (see FIG. 2).

TA1551 and TA1549 are both resistant to *Botrytis* and both lines contain introgression segments from *L. hirsutum* on chromosome 10. This indicates that resistance to *Botrytis* is located in the overlap region of the introgression lines TA1551 and TA1549 (see FIG. 2). Specifically, resistance to *Botrytis* is located between molecular markers defining the upper end of the homozygotic *L. hirsutum* introgression segment in TA 1551 in the region of marker CT66 and markers defining the lower end of the introgression segment in TA 1551 in the region of the marker CT95.

All abstracts, references, patents and published patent applications referred to herein are hereby incorporated by reference.

The present invention is illustrated by way of the foregoing description and examples. The foregoing description is intended as a non-limiting illustration, since many variations will become apparent to those skilled in the art in view thereof.

Changes can be made to the composition, operation and arrangement of the method of the present invention described herein without departing from the concept and scope of the invention.

What is claimed is:

1. A *Botrytis* resistant *Lycopersicon esculentum* tomato plant, or a part thereof, wherein said tomato plant, or a part thereof, comprises a chromosome 10 comprising:
   i. a *Lycopersicon hirsutum* introgression segment conferring *Botrytis* resistance and comprising a *Lycopersicon hirsutum* marker selected from the group consisting of TG408, CT20, and markers within the segment bounded by TG408 and CT20;
   ii. an upper region comprising *Lycopersicon esculentum* molecular marker TG280; and
   iii. a lower region comprising a *Lycopersicon esculentum* molecular marker selected from the group consisting of: CD72 and CD34A.

2. The tomato plant, or a part thereof, of claim 1, wherein the *Botrytis* resistance of said tomato plant is selected from the group consisting of: stem resistance, leaf resistance, flower resistance and fruit resistance.

3. The tomato plant, or a part thereof, of claim 1, wherein said tomato plant is an inbred.

4. The tomato plant, or a part thereof, of claim 1, wherein said *L. hirsutum* introgression segment is homozygous.

5. The tomato plant, or a part thereof, of claim 1, wherein said upper region is homozygous.

6. The tomato plant, or a part thereof, of claim 1, wherein said lower region is homozygous.

7. The tomato plant, or a part thereof, of claim 1, wherein said *L. hirsutum* introgression segment comprises an upper end comprising molecular marker TG408 and a lower end comprising molecular marker CT20.

8. The tomato plant, or a part thereof, of claim 1, wherein said part is selected from the group consisting of an embryo, a pollen, an ovule, a flower, a leaf, a seed, a root, a root tip, a stem, and a fruit.

9. The tomato plant, or a part thereof, of claim 1, wherein said tomato further comprises one or more introgressions from *Lycopersicon cerasiforme, Lycopersicon Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* or *Solanum lycopersicoides*.

10. A *Botrytis* resistant *Lycopersicon esculentum* tomato plant, or a part thereof, wherein said tomato plant, or a part thereof, comprises a chromosome 10 comprising:
   i. a *Lycopersicon hirsutum* introgression segment comprising an upper end comprising molecular marker TG408 and a lower end comprising molecular marker CT20;
   ii. an upper region comprising *Lycopersicon esculentum* molecular marker TG280; and
   iii. a lower region comprising a *Lycopersicon esculentum* molecular marker selected from the group consisting of: CD72 and CD34A.

11. The tomato plant, or a part thereof, of claim 10, wherein the *Botrytis* resistance of said tomato plant is selected from the group consisting of: stem resistance, leaf resistance, flower resistance and fruit resistance.

12. The tomato plant, or a part thereof, of claim 10, wherein said tomato plant is a hybrid.

13. The tomato plant, or a part thereof, of claim 10, wherein said tomato plant is an inbred.

14. The tomato plant, or a part thereof, of claim 10, wherein said *L. hirsutum* introgression segment is homozygous.

15. The tomato plant, or a part thereof, of claim 10, wherein said upper region is homozygous.

16. The tomato plant, or a part thereof, of claim 10, wherein said lower region is homozygous.

17. The tomato plant, or a part thereof, of claim 10, wherein said part is selected from the group consisting of an embryo, a pollen, an ovule, a flower, a leaf, a seed, a root, a root tip, a stem, and a fruit.

18. The tomato plant, or a part thereof, of claim 10, wherein said tomato further comprises one or more introgressions from *Lycopersicon cerasiforme, Lycopersicon pimpinellifalium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* or *Solanum lycopersicoides*.

* * * * *